United States Patent [19]

Gramlich et al.

[11] Patent Number: 5,081,309
[45] Date of Patent: Jan. 14, 1992

[54] PREPARATION OF 2-ALKYLCYCLOPENTANONES

[75] Inventors: Walter Gramlich, Edingen-Neckarhausen; Wolfgang Lengsfeld, Limburgerhof, both of Fed. Rep. of Germany

[73] Assignee: BASF Aktiengesellschaft, Ludwigshafen, Fed. Rep. of Germany

[21] Appl. No.: 65,096

[22] Filed: Jun. 22, 1987

Related U.S. Application Data

[63] Continuation of Ser. No. 833,257, Feb. 27, 1986, abandoned.

[30] Foreign Application Priority Data

Mar. 9, 1985 [DE] Fed. Rep. of Germany ....... 3508420

[51] Int. Cl.$^5$ .............................................. C07C 45/75
[52] U.S. Cl. .............................................. 568/345
[58] Field of Search ........................................ 568/345

[56] References Cited

U.S. PATENT DOCUMENTS

| | | | |
|---|---|---|---|
| 2,288,308 | 6/1942 | Warner | 568/390 |
| 3,701,798 | 10/1972 | Snapp et al. | 569/390 |
| 3,829,495 | 8/1974 | Mizutani et al. | 260/586 R |
| 4,049,571 | 9/1977 | Nissen et al. | 568/390 |
| 4,146,581 | 3/1979 | Nissen et al. | 264/586 C |
| 4,212,825 | 7/1980 | Nissen et al. | 568/390 |
| 4,270,006 | 5/1981 | Heilen et al. | 568/396 |
| 4,289,911 | 9/1981 | Isogai et al. | 568/396 |
| 4,374,274 | 2/1983 | Heilen et al. | 568/345 |

FOREIGN PATENT DOCUMENTS

| | | | |
|---|---|---|---|
| 13385 | 7/1980 | European Pat. Off. | |
| 100019 | 2/1984 | European Pat. Off. | |
| 127835 | 5/1984 | European Pat. Off. | |
| 28703 | 10/1984 | European Pat. Off. | |
| 633595 | 7/1936 | Fed. Rep. of Germany | |
| 3319430 | 11/1984 | Fed. Rep. of Germany | 568/390 |
| 2056450 | 5/1971 | France | |

OTHER PUBLICATIONS

*Azerb. Neft. Khoz.*, vol. 9 (1975), pp. 69–79.
*Chem. Pharm. Bull.*, vol. 20, No. 1 (1972), pp. 197–201.
*Chem. Pharm. Bull.* vdol. 21, No. 1 (1973), pp. 215–219.
*Chem. Ber.* 29 (1986), p. 1836.
*Synthesis*, May, 1976, pp. 315–318.
*J. Indian Chem. Sor.*, vol. 30, No. 1, pp. 23–25 (1953).

Primary Examiner—James H. Reamer
Attorney, Agent, or Firm—Oblon, Spivak, McClelland, Maier & Neustadt

[57] ABSTRACT

Cyclopentanones monoalkylated in the 2-position and of the general formula I

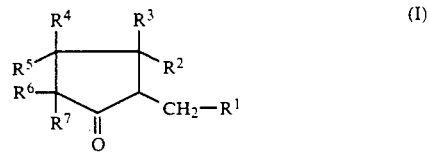

where $R^1$ is a branched or straight-chain aliphatic group of 2 to 12 carbon atoms and $R^2$ to $R^7$ may be identical or different and are each hydrogen or alkyl of 1 to 5 carbon atoms, are prepared by a process in which a cyclopentanone of the general formula II

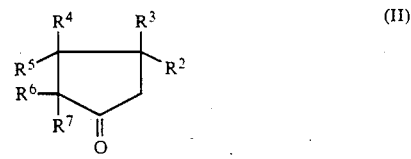

or a corresponding cyclopentenone, is reacted with an aldehyde of the general formula III

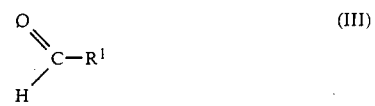

at from 80° to 280° C. in the presence of hydrogen in an autoclave, over a catalyst which contains, as active components, on the one hand an oxide or a phosphate of magnesium, aluminum, titanium or zinc or of one of the rare earth metals, and on the other hand a noble metal of group VIII of the periodic table, preferably palladium.

The 2-alkylcyclopentanones obtainable according to the invention in a simple single-stage reaction with virtually complete conversion and high selectivity are important as intermediates and in particular as scents.

16 Claims, No Drawings

PREPARATION OF 2-ALKYLCYCLOPENTANONES

This application is a Continuation of Ser. No. 06,833,257, filed on Feb. 27, 1986, now abandoned.

The present invention relates to a process for the preparation of cyclopentanones which are monoalkylated in the α-position, the process being substantially better than the prior art.

The introduction of alkyl groups into the α-position of the basic cyclopentanone skeleton is known per se.

For example, M. Hajak et al. (cf. Synthesis 1976, pages 315-318) follow a synthesis route in which cyclopentanone is reacted with an alk-1-ene, such as oct-1-ene, in the presence of lead(IV) oxide, manganese(IV) oxide or copper oxide and a small amount of acetic acid to give an α-alkylated cyclopentanone, such as 2-octylcyclopentanone. According to the authors, the yields obtained in this process vary from 64 to 77%.

Using a process based on the same principles, S. D. Mekhtiev et al. (cf. Azerb. Neft. Khoz. 9 (1975), 69-79) obtained 2-heptylcyclopentanone in a yield of only 53% of theory in the reaction of cyclopentanone with hept-1-ene, in spite of optimization measures.

The alkylation of cyclopentanone with an alkyl halide in the presence of a base is also known. For example, Gupta et al. (cf. J. Ind. Chem. Soc. 30 (1953), 23-25) describe the alkylation of cyclopentanone with an alkyl bromide, e.g. heptyl bromide, in the presence of sodium amide. However, because of the large number of by-products, it was impossible to isolate the resulting 2-heptylcyclopentanone in pure form in this procedure.

K. Takahashi (cf. Chem. Pharm. Bull. 20 (1972) 197-201) overcame the problem of polyalkylation by a procedure in which the cyclopentanone was first converted to the enamine with morpholine in the presence of p-toluenesulfonic acid in a benzene as the solvent by removing the water formed in the reaction, and the enamine was then reacted with an alkenyl bromide to give the corresponding alkenylcyclopentanone in a yield of 46-59%. It was then necessary to hydrogenate the unsaturated compound in the presence of a catalyst, in a third stage, to give the alkylcyclopentanone. The disadvantage of this process is that three steps are required and the yields are unsatisfactory.

The process due to A. Jjima and K. Takahashi (cf. Chem. Pharm. Bull. 21 (1973) 215-219) also involved the detour via the enamine obtainable from cyclopentanone and morpholine.

In this process, cyclopentanone and morpholine first had to be heated at the boil for 12 hours in the presence of p-toluenesulfonic acid in benzene in order to separate off the water formed in the reaction. The mixture was then stirred for one hour with dilute hydrochloric acid, after which the phases were separated, the aqueous phase was extracted once again with benzene, the combined phases were washed with 5% strength NaHCO₃ solution and water, the benzene was distilled off and the residue was fractionated.

The resulting enamine was again refluxed in a second stage with the aldehyde for 12 hours, in benzene as a solvent. The cooled solution was then acidified with dilute hydrochloric acid, stirred for 1 hour and extracted with benzene, the benzene extract was washed with water, the benzene was distilled off completely and the residue was fractionated. The alkylidenecyclopentanones were obtained in a yield of 40-75% in this way.

In a third stage, the alkylidene compounds were then hydrogenated in the presence of a hydrogenation catalyst to give the α-alkylcyclopentanones. The disadvantage of this process is that it consists of three steps, some of which are very tedious, and that it gives only moderate yields. Furthermore, a preparation process which employs amines is not very advisable because the alkylated cyclopentanones are for the major part used as scents and therefore have to meet very high requirements in respect of their olfactory properties.

It is also known that cyclopentanone can be reacted directly with an aldehyde in the presence of a basic catalyst (cf. German Patent 633,595 of 1933).

The yields obtained in this process are from 23.3 to 45.2%. The main by-products, as described long ago by, inter alia, Vorländer in Chem. Ber. 29 (1896), 1836, are the cyclopentanones condensed with two molecules of aldehyde. Although the subsequent catalytic hydrogenation gives yields of from 90 to 95% of α-alkylcyclopentanones, the entire process cannot be considered economical.

It is an object of the present invention to provide a more economical process for the preparation of the 2-alkylcyclopentanones, which provide valuable scents, the said process being free of the disadvantages of the known processes, i.e. permitting the preparation of the 2-alkylcyclopentanones in good yields in a simple single-stage procedure.

We have found that this object is achieved and that, surprisingly, cyclopentanones which are unsubstituted α to the keto group can be reacted with a large number of aliphatic aldehydes with virtually complete conversion and in high selectivity by a single-stage reaction to give the desired α-monoalkylated cyclopentanones, if the reactants are reacted at from 80° to 280° C. in the presence of hydrogen in an autoclave, over a catalyst which contains one component for catalytic condensation and a second component for catalytic hydrogenation.

The present invention accordingly relates to a process for the preparation of cyclopentanones which are monoalkylated in the 2-position and of the general formula I

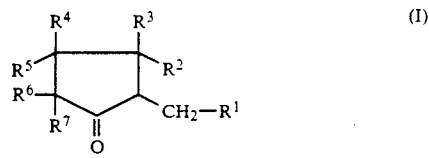

where R¹ is a branched or straight-chain aliphatic group of 2 to 12, preferably 4 to 8, carbon atoms, and R² to R⁷ may be identical or different and are each hydrogen or alkyl of 1 to 5 carbon atoms, preferably hydrogen or methyl, wherein a cyclopentanone of the general formula II

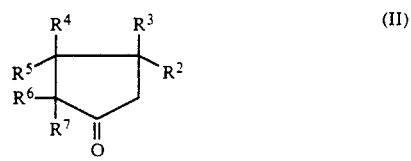

or a corresponding cyclopentanone, is reacted with an aldehyde of the general formula III

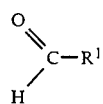

(III)

where $R^1$ has the above meanings, at from 80° to 280° C., preferably from 100° to 200° C., in the presence of hydrogen in an autoclave, over a catalyst which contains, as active components, on the one hand an oxide or a phosphate of magnesium, aluminum, titanium or zinc or of a rare earth metal, and on the other hand a noble metal of group VIII of the periodic table, preferably palladium.

The process takes place in a particularly advantageous manner if the reaction is carried out under a hydrogen pressure of from 1 to about 300, preferably from 10 to about 100, in particular from 10 to 50, bar.

In a very advantageous embodiment of the process, the reaction is carried out in the absence of substantial amounts of a solvent, since this substantially improves the space-time yields and facilitates working up, without reducing the yield.

The high selectivities of the novel process are achieved even when $R^6$ and $R^7$ are each hydrogen, i.e. when α,α-unsubstituted cyclopentanones are employed.

The selectivities obtained are surprising in that, under the reaction conditions used, both autocondensation of the cyclopentanone and autocondensation of the aldehyde used, and heteroaldol polycondensations (1 molecule of 2-alkylcyclopentanone with a further molecule of aldehyde to give 2,5-dialkylcyclopentanones), could have occurred.

As shown in the Examples below, the abovementioned side reactions are virtually completely absent in the reaction according to the invention.

The novel process is carried out in an autoclave in general by initially taking all the components, i.e. cyclopentanone of the formula II or the corresponding cyclopentanone, an aldehyde of the formula III and the heterogeneous catalyst, closing the autoclave and then flushing it first with nitrogen and thereafter with hydrogen. The mixture is then heated to the reaction temperature while hydrogen is forced in.

In a particularly advantageous procedure, flushing with hydrogen is carried out and hydrogen is then forced into the autoclave to a hydrogen pressure of 2-20 bar, after which the temperature is increased, and the hydrogen pressure is raised to 40-50 bar when the reaction temperature is reached. In this procedure, both the aldol condensation and the subsequent hydrogenation take place in one step, the hydrogen consumed being replaced continuously.

When the reaction is complete, the autoclave is cooled, the pressure is let down and the reacted mixture is sucked out via a filter and thus separated off from the catalyst. The catalyst can be flushed back into the autoclave with fresh starting materials through the same filter and used for the next batch. Alternatively, the catalyst may be left in the autoclave by using a siphon tube of appropriate length and equipped with a frit for discharging the liquid phase. The catalyst can be employed several times. The resulting liquid mixture discharged from the reactor only requires to be distilled. If necessary, the water formed during the reaction can be removed as the lower phase prior to distillation.

This batchwise procedure described is suitable for reactions on a fairly small industrial scale. For large-scale industrial production, however, the catalyst, in the form of a supported catalyst, for example in the form of spheres or extrudates, may be installed as a fixed bed in a reactor column, and the mixture of cyclopentanone or cyclopentanone and aldehyde pass continuously over the catalyst under the conditions according to the invention.

As stated above, catalyst according to the invention is in principle a catalyst system consisting of two components.

One component is used for the condensation step. Suitable components for this step are the oxides or phosphates of magnesium, aluminum, titanium or zinc or of one of the rare earths, such as praseodymium oxide ($Pr_4O_6$). The oxides of aluminum have proven particularly useful and advantageous.

The catalyst contains, as a second component, a noble metal of group VIII of the periodic table, in particular palladium.

The other noble metals, i.e. platinum, ruthenium, rhodium, iridium and osmium, can also be used but, for economic reasons, are generally less suitable.

The catalyst may be in the form of a mixture of the condensation catalyst, e.g. $Al_2O_3$ and the hydrogenation catalyst, such as palladium on active carbon, or in the form of a homogeneous catalyst, for example one which contains palladium on $Al_2O_3$. The only important factor is that both catalyst components are present simultaneously.

The content of noble metal is in general from 0.1 to 5% by weight. Catalysts which contain palladium as the noble metal in an amount of from 0.5 to 1%, based on the amount of catalyst used, are preferred.

In the batchwise procedure, suspension catalysts are used. If the reaction is carried out continuously in a reactor column, it is preferable to use supported catalysts on which the noble metal, e.g. palladium, is applied. The carrier, which consists of the condensation component, can be impregnated with an aqueous solution which contains a palladium salt, such as palladium nitrate.

The palladium metal is then formed automatically under the hydrogenation conditions, although it is also possible to subject the catalyst to a separate hydrogenation step for this purpose. The catalyst used in the continuous procedure can be in the form of tablets, granules, spheres or extrudates, while the powder form is frequently used in the batchwise procedure.

Examples of suitable cyclopentanones of the general formula II are cyclopentanone, 3-methylcyclopentanone, 2-methylcyclopentanone, 3,4-dimethylcyclopentanone, 2,4-dimethylcyclopentanone, 2,3-dimethylcyclopentanone, 2,3,4-trimethylcyclopentanone, 2,2,4-trimethylcyclopentanone, 2,2,3-trimethylcyclopentanone and 2,2,4-trimethylcyclopentanone. Cyclopentanone is preferably employed since its derivatives obtainable according to the invention are particularly important.

However, it is also possible to use the corresponding cyclopentanones, such as 3-methylcyclopent-2-enone, and the double bond present is also hydrogenated under the reaction conditions, as is the double bond formed during the condensation. The double bond may be in any position; in this case, $R^2$ or $R^2$ and $R^4$ or $R^4$ and $R^6$ correspond to a double bond.

Suitable aldehydes of the formula III are both the straight-chain unsubstituted aldehydes, such as propanal, butanol, pentanal, hexanal, heptanal, octanal, nonanal, decanal, undecanal and dodecanal, and various branched and substituted aldehydes, e.g. 2-methylpropanal, 2-methylbutanal, 2-methylpentanal, 2-methylhexanal, 2-methylheptanal, 2-methyloctanal, 2-methylnonanal, 2-methyldecanal, 2-methylundecanal, 3-methylbutanal and 3-methylpentanal.

The molar ratio of the cyclopentanone to the aldehyde can be 1:1, although it is preferable to use an excess of the cheaper reactant; this permits a substantial increase in the selectivity based on the more expensive reactant.

It is advantageous to carry out the reaction in the absence of a solvent. However, a solvent such as methanol, ethanol or propanol may be employed.

The reaction temperature for the novel process depends on the starting components and the type and amount of the catalyst used, and may vary from 80° to 280° C. When large amounts of catalyst are used, the reaction temperature may be below 80° C. The preferred temperature for an economical process is from 100° to 200° C. The amount of catalyst used varies depending on the reactivity of the aldehyde and cyclopentanone derivative. From 3 to 8% by weight, based on the sum of the starting compounds, are preferably used.

The hydrogen pressure, too, can be varied within wide limits and depends on the content of the noble metal used. Where a catalyst which has been used frequently and contains 0.5% by weight of palladium on alumina (cf. Example 1) is employed, a hydrogen pressure of from 40 to 50 bar is sufficient when 5% by weight of catalyst are employed. When a catalyst having a higher palladium content is used or larger amounts of the above 0.5% strength $Pd/Al_2O_3$ catalyst are employed, lower hydrogen pressures are sufficient.

The novel process can be used to react cyclopentanones which are unsubstituted α to the keto group, or the corresponding cyclopentanones, with a large number of aliphatic aldehydes in a simple single-stage reaction with virtually complete conversion and in high selectivity to give the valuable α-monoalkylated cyclopentanones. However, the process according to the invention is distinguished not only by better yields and better space-time yields but also by the fact that it causes little pollution since it is carried out in the absence of auxiliary bases or salts and only in the presence of a heterogeneous catalyst, so that no salt-containing effluents are produced.

A particularly important industrial product of the novel process is 2-heptylcyclopentanone, which is an important jasmine-type scent. However, a large number of other 2-substituted cyclopentanones are also useful scents (cf. Perfumer and Flavorist 8 (1983), April/May issue, pages 68-74).

EXAMPLE 1

Preparation of 2-heptylcyclopentanone

A mixture of 1000 ml (930 g; 11 moles) of cyclopentanone, 500 ml (425 g, 3.7 moles) of n-heptanal and 70 g of a pulverulent catalyst containing 0.5% by weight of palladium on alumina was initially taken in an autoclave. The autoclave was flushed with nitrogen and hydrogen, after which hydrogen was forced in to a pressure of 10 bar at 25° C. and the mixture was then heated for 3 hours at 110° C. under a hydrogen pressure of 35 bar and finally at 160° C. under a hydrogen pressure of 50 bar until the pressure remained constant. This took about 10 hours. The catalyst was separated of and the mixture discharged from the reactor was then directly fractionated.

After the light ends (605 g of cyclopentanone at a boiling point of 130° C. and 5 g of an intermediate fraction) had been distilled off, 633 g (3.48 moles) of pure 2-heptylcyclopentanone (bp. 93° C./1 mbar) were obtained, corresponding to a selectivity of 94%, based on n-heptanal. The selectivity with respect to cyclopentanone was 92° C.

EXAMPLE 2

Preparation of 2-hexylcyclopentanone

A mixture of 1008 g (12 moles) of cyclopentanone, 800 g (8 moles) of n-hexanal and 80 g of a pulverulent catalyst containing 0.5% by weight of palladium on alumina was hydrogenated in an autoclave at 140° C. and under a hydrogen pressure of 70 bar until the pressure remained constant (about 15 hours), the procedure used being similar to that described in Example 1. The catalyst was separated off and the mixture discharged from the reactor was then distilled directly. 294 g (3.5 moles) of cyclopentanone were recovered as fraction 1. 1103 g of pure 2-hexylcyclopentanone (bp. 84° C./0.35 mbar) were obtained as the main fraction; this corresponded to a selectivity of 82%, based on n-hexanal. When, as in Example 1, the molar ratio of cyclopentanone to hexanal was increased to 3:1, the selectivity increased to above 90%, as in the case of 2-heptylcyclopentanone.

EXAMPLE 3

Preparation of 2-(2-methylpentyl)-cyclopentanone

A mixture of 126 g (1.5 moles) of cyclopentanone, 50 g (0.5 mole) of 2-methylpentanal and 10 g of a pulverulent catalyst containing 1% by weight of palladium, 94% by weight of alumina and 5% by weight of praseodymium oxide was initially taken in a 300 ml autoclave. The autoclave was flushed with nitrogen and hydrogen at 20° C., after which $H_2$ was forced in to a pressure of 10 bar and the reaction mixture was then heated at 150° C. under a hydrogen pressure of 30 bar until the pressure remained constant. The catalyst was removed, after which the mixture discharged from the autoclave was fractionated. 74.9 g of pure 2-(2-methylpentyl)-cyclopentanone (bp. 125° C./20 mbar) were obtained, corresponding to a selectivity of 89.2%, based on 2-methylpentanal.

We claim:

1. A process for the preparation of a cyclopentane which is monoalkylated at the 2-position and having the formula I:

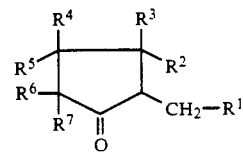

wherein $R^1$ is a branched or straight-chain aliphatic group of 2-12 carbon atoms and $R^2$, $R^3$, $R^4$, $R^5$, $R^6$ and $R^7$, which are identical or different, are each hydrogen or an alkyl group of 1-5 carbon atoms, which comprises reacting a cyclopentanone of the formula II:

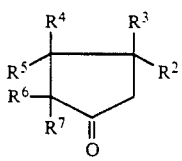

or a corresponding cyclopentanone thereof, with an aldehyde of the formula III:

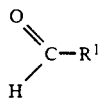

wherein $R^1$ is as defined above, at from 80°-280° C., in the presence of hydrogen in an autoclave, over a catalyst which contains a condensation catalyst selected from the group consisting of an oxide or a phosphate of magnesium, aluminum, titanium, zinc and a rare earth metal, and a hydrogenation catalyst of a Group VIII noble metal selected from the group consisting of palladium, platinum, ruthenium, rhodium, iridium and osmium.

2. The process as claimed in claim 1, wherein the reaction is carried out under a hydrogen pressure of from 1 to about 300 bar.

3. The process as claimed in claim 1, wherein the reaction is carried out in the absence of substantial amounts of a solvent.

4. The process as claimed in claim 1, wherein the mixture of the starting compounds and catalyst is initially placed in the autoclave, and the latter is closed, flushed with an inert gas and then with hydrogen, and then heated at the reaction temperature while hydrogen is forced thereinto.

5. The process as claimed in claim 1, wherein the autoclave is flushed with hydrogen, after which hydrogen is forced into the autoclave to a hydrogen pressure of from 2 to 20 bar, the temperature is then increased, and the hydrogen pressure is raised when the reaction temperature is reached.

6. The process as claimed in claim 1, wherein $R^1$ is a branched or straight-chain aliphatic group of 2-12 carbon atoms.

7. The process as claimed in claim 1, wherein $R^2$, $R^3$, $R^4$, $R^5$, $R^6$ and $R^7$ are each hydrogen or a methyl group.

8. The process as claimed in claim 1, wherein said hydrogenation catalyst is palladium.

9. The process as claimed in claim 1, wherein said reaction is carried out at a hydrogen pressure of from 10-100 bar.

10. The process as claimed in claim 1, wherein $R^6$ and $R^7$ are each hydrogen.

11. The process as claimed in claim 5, wherein after the temperature is increased, the hydrogen pressure is increased from a pressure in the range of 2-20 bar to a pressure in the range of 40-50 bar.

12. The process as claimed in claim 1, wherein the cyclopentane of the formula II is selected from the group consisting of cyclopentanone, 3-methylcyclopentanone, 2-methylcyclopentanone, 3,4-dimethylcyclopentanone, 2,4-dimethylcyclopentanone, 2,3-dimethylcyclopentanone, 2,3,4-trimethylcyclopentanone, 2,2,4-trimethylcyclopentanone, 2,2,3-trimethylcyclopentanone and 2,2,4-trimethylcyclopentanone.

13. The process as claimed in claim 1, wherein said corresponding cyclopentanone is such that $R^2$, or $R^2$ and $R^4$, or $R^4$ and $R^6$ correspond to a double bond.

14. The process as claimed in claim 1, wherein said aldehyde of the formula III is a straight-chain unsubstituted aldehyde selected from the group consisting of propanol, butanal, pentanal, hexanal, heptanal, octanal, nonanal, decanal, undecanal and dodecanal; and a branched and substituted aldehyde selected from the group consisting of 2-methylpropanol, 2-methylbutanal, 2-methypentanal, 2-methylhexanal, 2-methylheptanal, 2-methyloctanal, 2-methylnonanal, 2-methyldecanal, 2-methylundecanal, 3-methylbutanal and 3-methylpentanal.

15. The process as claimed in claim 1, wherein said cyclopentanone of the formula I is 2-heptylcyclopentanone.

16. A process for the preparation of a cyclopentanone which is monoalkylated at the 2-position and having the formula I:

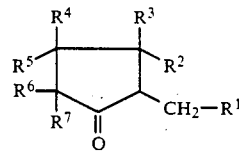

wherein $R^1$ is a branched or straight-chain aliphatic group of 2-12 carbon atoms and $R^2$, $R^3$, $R^4$, $R^5$, $R^6$ and $R^7$, which are identical or different, are each hydrogen or an alkyl group or 1-5 carbon atoms, which comprises reacting a cyclopentanone of the formula II:

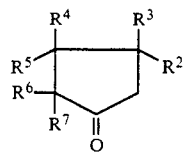

or a corresponding cyclopentenone thereof, with an aldehyde of the formula III:

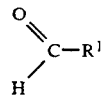

wherein $R^1$ is as defined above, at from 80°-280° C., in the presence of hydrogen in an autoclave, over a catalyst which contains a condensation catalyst of an oxide of aluminum, and a hydrogenation catalyst of a Group VIII noble metal selected from the group consisting of palladium, platinum, ruthenium, rhodium, iridium and osmium.

* * * * *